(12) United States Patent  
Thompson et al.

(10) Patent No.: US 6,675,049 B2  
(45) Date of Patent: Jan. 6, 2004

(54) METHOD AND APPARATUS FOR AUTOMATIC IMPLANTABLE MEDICAL LEAD RECOGNITION AND CONFIGURATION

(75) Inventors: David L. Thompson, Andover, MN (US); Steven D. Goedeke, Forest Lake, MN (US); Gregory J. Haubrich, Champlin, MN (US); Ryan Cobian, New Brighton, MN (US); Eric Bonde, Victoria, MN (US); John L. Sommer, Coon Rapids, MN (US); Jonathan Werder, Maple Grove, MN (US); Nels Nerison, Wyoming, MN (US); Eric V. Blaha, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 46 days.

(21) Appl. No.: 09/907,308

(22) Filed: Jul. 17, 2001

(65) Prior Publication Data

US 2003/0018369 A1 Jan. 23, 2003

(51) Int. Cl.⁷ ................................................. A61N 1/36
(52) U.S. Cl. .......................................... 607/60; 607/59
(58) Field of Search ............................. 607/60, 32, 30, 607/31, 59; 128/903

(56) References Cited

U.S. PATENT DOCUMENTS

| 3,348,548 | A | 10/1967 | Chardack |
| 3,754,555 | A | 8/1973 | Schmitt |
| 3,814,104 | A | 6/1974 | Irnich et al. |
| 3,844,292 | A | 10/1974 | Bolduc |
| 3,974,834 | A | 8/1976 | Kane |
| 4,374,382 | A | 2/1983 | Markowitz |
| 4,485,813 | A | 12/1984 | Anderson et al. |
| 4,543,955 | A | 10/1985 | Schroeppel |
| 4,556,063 | A | 12/1985 | Thompson et al. |
| 4,628,934 | A | 12/1986 | Pohndorf et al. |
| 4,730,188 | A | 3/1988 | Milheiser |
| 4,821,723 | A | 4/1989 | Baker, Jr. et al. |

(List continued on next page.)

FOREIGN PATENT DOCUMENTS

| EP | 0 317 986 | 10/1993 |
| WO | WO 98/43700 | 3/1998 |

*Primary Examiner*—George R. Evanisko  
(74) *Attorney, Agent, or Firm*—Girma Wolde-Michael; Elisabeth L. Belden

(57) ABSTRACT

An automated identification and configuration system for use with an implantable medical device (IMD) is disclosed. The system includes a first communication circuit that is attached to, or otherwise carried by, a detachable component associated with the IMD such as a medical lead. The communication circuit stores data such as model numbers, serial numbers, technical data, and/or calibration information that describes the additional component. This information may be transferred by the first communications circuit to a second communications circuit that is external to the additional component. This transferred data can be used to automatically configure the internal circuitry and connection functions of the IMD to properly interface with, and support, the additional component. For example, the data can be used to automatically adjust amplifier gains or other sensor circuitry, or to configure a connector block to properly couple to the component. The data may further be entered into a patient record on an external programmer, or may be transferred to a central storage location to be generally accessible to health care providers. In one embodiment, the first communication circuit is a passive RF transponder. This first communication circuit may include a receiver as well as a transmitter to allow the circuit to programmably receive data at the time of component manufacture.

18 Claims, 7 Drawing Sheets

U.S. PATENT DOCUMENTS

| | | |
|---|---|---|
| 5,025,550 A | 6/1991 | Zirbes et al. |
| 5,041,826 A | 8/1991 | Milheiser |
| 5,052,388 A | 10/1991 | Sivula et al. |
| 5,127,404 A | 7/1992 | Wyborny et al. |
| 5,131,388 A | 7/1992 | Pless et al. |
| 5,144,524 A | 9/1992 | Tullis et al. |
| 5,144,949 A | 9/1992 | Olson |
| 5,154,170 A | 10/1992 | Bennett et al. |
| 5,158,078 A | 10/1992 | Bennett et al. |
| 5,166,676 A | 11/1992 | Milheiser |
| 5,199,428 A | 4/1993 | Obel et al. |
| 5,207,218 A | 5/1993 | Carpentier et al. |
| 5,246,014 A | 9/1993 | Williams et al. |
| 5,252,962 A | 10/1993 | Urbas et al. |
| 5,271,395 A | 12/1993 | Wahlstrand et al. |
| 5,281,855 A | 1/1994 | Hadden et al. |
| 5,312,453 A | 5/1994 | Shelton et al. |
| 5,314,430 A | 5/1994 | Bardy |
| 5,330,507 A | 7/1994 | Schwartz |
| 5,331,966 A | 7/1994 | Bennett et al. |
| 5,354,316 A | 10/1994 | Keimel |
| 5,374,279 A | 12/1994 | Duffin, Jr. et al. |
| 5,397,343 A | 3/1995 | Smits |
| 5,423,334 A | 6/1995 | Jordan |
| 5,499,017 A | 3/1996 | Beigel |
| 5,534,018 A | 7/1996 | Wahlstrand et al. |
| 5,545,186 A | 8/1996 | Olson et al. |
| 5,626,630 A | 5/1997 | Markowitz et al. |
| 5,782,891 A | 7/1998 | Hassler et al. |
| 5,824,030 A | 10/1998 | Yang et al. |
| 5,833,603 A * | 11/1998 | Kovacs et al. .............. 600/317 |
| 5,919,221 A | 7/1999 | Miesel |
| 6,016,447 A | 1/2000 | Juran et al. |
| 6,085,118 A | 7/2000 | Hirschberg et al. |
| 6,178,355 B1 | 1/2001 | Williams et al. |
| 6,409,674 B1 * | 6/2002 | Brockway et al. .......... 600/486 |

* cited by examiner

METHOD AND APPARATUS FOR AUTOMATIC IMPLANTABLE MEDICAL LEAD RECOGNITION AND CONFIGURATION

BACKGROUND OF THE INVENTION

1. Field of the Invention

The present invention relates generally to implantable medical devices; and, more particularly, to a method and apparatus to automatically identify multiple leads and their proper connection to an implantable medical device such as a pacemaker or cardioverter/defibrillator.

2. Background Art

An implantable intravascular lead assembly is often implanted within a patient's body to provide electrical stimulation to the heart. Such lead assemblies may include one or more electrical conductors that are adapted to be suitably connected to a source of electrical energy, which may be a pacemaker or cardioverter/defibrillator. The electrical conductor, in turn, includes an electrode tip that engages the endocardial or epicardial tissue of the heart to provide stimulation and sensing capabilities. The lead assembly may be intravenously inserted through a body vessel, such as a vein, into one or more cardiac chambers, or alternatively, attached to the epicardial surface of the heart. The conductor is sealed from body fluids by a biocompatible and bio-stable insulating material.

In a typical lead assembly, the electrode tip is firmly lodged in, and permanently secured to, the endothelial lining or epicardial surface of the heart. These lead assemblies are referred to as an endocardial or epicardial lead, respectively. Some examples of conventional endocardial and epicardial leads may be found in U.S. Pat. No. 3,348,548 to Chardack, U.S. Pat. No. 3,754,555 to Schmitt, U.S. Pat. No. 3,814,104 to Irnich et al., U.S. Pat. No. 3,844,292 to Bolduc, U.S. Pat. No. 3,974,834 to Kane, U.S. Pat. No. 5,246,014 to Williams, and U.S. Pat. No. 5,397,343 to Smits. A representative defibrillation lead is described in U.S. Pat. No. 6,178,355 to Williams.

With the increased use of multi-chamber pacemakers and defibrillators such as those that provide bi-atrial or bi-ventricular pacing capabilities, multiple leads are required to deliver electrical stimulation to various locations within the heart. With the use of multiple leads that are positioned within one or more small vessels of the body, it has become even more important to minimize lead and lead connector size. As leads become smaller, it becomes increasingly difficult to mark leads with the appropriate identification, including manufacturer identification and/or lead model and serial numbers. This may make it more difficult for a physician to determine which lead is to be inserted into a given port of an implantable medical device (IMD) during an implant procedure.

One solution to providing marking information on lead systems is described in U.S. Pat. No. 5,824,030 to Yang. This patent discloses a single-pass transvenous lead for atrial sensing and pacing, ventricular sensing and pacing, as well as for ventricular and atrial defibrillation. Visual indicators are provided on the lead to identify which one of several distal electrode pairs are being used.

Another solution to properly configuring the leads of an IMD is disclosed in U.S. Pat. No. 5,374,279 to Duffin. The described medical electrical pulse generator includes a switchable connector assembly. The connector assembly is provided with connector bores that are each adapted to receive a medical electrical lead. Electrical connectors located within the bores are arranged such that interconnection of the pulse generator circuitry and the configuration of the electrodes on the leads and/or housing of the device can be altered by means of connector pins.

Yet another method of attaching multiple electrode leads to an IMD is described in U.S. Pat. No. 4,628,934 to Pohndorf. The '934 patent describes an electronic electrode switching circuit that minimizes the number of feedthroughs from a pacer case to a pacer neck that are needed to couple to the pacing lead electrodes. These feedthroughs can be selectively connected to a desired electrode by the physician at the time of initial implantation or any time thereafter. The electronic connection to a feedthrough may be dedicated to a single electrode or electrode pair, or alternatively, the electrodes may be electronically sampled by circuitry in the pacer. The electrode switching circuit may be located in the pacer neck, in an adapter between the pacer neck and a multielectrode lead, or in a multielectrode lead.

Another method for automatically configuring the multiple leads of an IMD is described in U.S. Pat. No. 6,085,118 to Hirschberg. The '118 patent describes an implantable cardiac stimulator with at least two terminals. Each terminal is connectable to an implantable electrode for delivering stimulation pulses to a heart, and/or for sensing cardiac activity signals. The stimulator also has a switch and a control unit which operates the switch, so that one or both terminals are connectable to the pulse generator. The control unit identifies a position status for at least one of the electrodes in response to a signal received at the time of implantation. Although the control unit may use a signal from an electrode to configure the switch, premature sensed events, artifacts and/or EMI may cause the control unit to incorrectly configure the system.

Another identification system is described in U.S. Pat. No. 5,300,120 to Knapp, which involves a passive transponder that may be encoded with a binary value that may be up to sixty-four bits long. This value may be read with a hand-held electromagnetic device that is located outside the body and in proximity to the transponder. The encoded information may include patient demographics, implant data, and manufacturer information.

Another similar mechanism for remotely monitoring device data is described in U.S. Pat. No. 5,626,630 to Markowitz. The disclosed telemetry system includes a remote monitoring station, a repeater worn externally by a patient, and a quasipassive transponder attached to a device implanted in the patient. The remote monitoring station communicates to the repeater to initiate an interrogation routine between the repeater and the transponder to extract patient condition information from the implanted device. When the repeater receives the condition information, it relays it to the remote monitoring station. The disclosed system does not automatically identify leads, calibrate lead-based sensors, or automatically configure leads and/or sensors to an IMD.

U.S. Pat. No. 5,833,603 to Kovacs describes another system for sensing one or more physiological signals within a living body to measure optical, mechanical, chemical, and/or electrochemical properties. The system includes a transponder for wirelessly transmitting data corresponding to the sensed parameter values to a remote reader. Disclosed embodiments utilize temperature sensors, strain sensors, pressure sensors, magnetic sensors, acceleration sensors, ionizing radiation sensors, acoustic wave sensors, chemical sensors, and photosensors. The disclosed system does not include means to automatically identify or configure leads, or to calibrate the lead-based sensors.

Another mechanism for identifying information related to the configuration of an IMD is disclosed in U.S. Pat. No. 5,423,334 to Jordan. The disclosed system provides a characterization tag for attachment to the IMD. The tag circuitry is selectively loaded to store data describing the IMD, and may be read by a probe located outside the body. The system does not store lead identification or configuration information.

Yet another system for storing and transmitting device information is described in U.S. Pat. No. 5,252,962 to Urbas. The disclosed device includes a sensor for use in transmitting a parameter such as temperature from within a living body to a device that is located outside the body. The IMD includes a programmable memory to store user ID data.

While the above publications teach various improvements to the art, they do not address the problem of identifying and configuring multiple leads and/or other implantable devices for use with an IMD.

SUMMARY OF THE INVENTION

It is a principal object of the present invention to provide an improved interface between conventional lead systems and IMDs.

Another object is to provide a system and method for automatically identifying leads and for enabling the proper connection of the identified leads to an IMD.

Another object is to provide a system and method for automatically receiving sensor calibration information for lead-based sensors.

Yet another object is to provide a system and method for automatically calibrating lead-based sensors.

Another object is to provide an IMD that automatically configures connections between one or more leads and respective IMD ports.

An additional object is to provide a connector block for electrically and mechanically coupling multiple leads or sensors to an electrical source of energy, such as a pacemaker, defibrillator or neuro stimulator.

Yet another object is to provide a system for use with an IMD that allows an additional component of the IMD to be automatically identified for purposes of system configuration.

It is a further object to provide a system for use with an IMD that stores patient data that may be transferred to a central location for use in performing diagnosis and therapy.

The current system and method addresses these and other objectives by providing a system for use with an active IMD (hereinafter, "IMD") such as a pacing device, or another external device. The system is capable of automatically identifying one or more additional implantable medical devices such as leads that may be associated with the IMD. In one embodiment, the invention includes a first communication circuit that is attached to, or integrated within, a lead. The communication circuit stores data such as model and serial numbers, technical information, and calibration data. At the time of implant or sometime thereafter, information stored by the first communication circuit may be transferred to a second communications circuit that is external to the lead. The second communications circuit may reside within the IMD, an external programmer, a personal data management (PDM) unit, or within any other unit such as a Personal Digital Assistant (PDA) that is located within a predetermined range of the first communication circuit. This transferred data can be used both to indicate the presence of the lead, and to identify lead type. Such information can be used, for example, to automatically configure the connector block of the IMD to properly couple to the lead. The data can further be used to automatically adjust amplifier gains or other circuitry associated with the lead. The data may be entered into a patient record on an external programmer, or may be transferred to a central storage location for use by health care providers when performing diagnosis and therapy associated with the IMD.

In another embodiment, the data provided by the first communications circuit includes identification and calibration information concerning additional components of the system. For example, physiologic sensors carried on the leads may be identified so that the IMD can enable and calibrate internal circuitry to receive the physiologic signals. This allows certain functions within the IMD to automatically be enabled only when a component is present in the system so that power can otherwise be conserved. Any other components of an IMD may be identified and calibrated by using a communication circuit according to the current invention. This may include implantable devices such as pluggable antennas, electrodes that can be selectively coupled to the IMD case, and any other types of components that may be selectively added to the system.

According to one aspect of the system, the first communication circuit may be a passively-powered RF transponder. The transponder receives power from an external source. Ultrasonic, optical, and electromagnetic power may be used to power the first communication circuit. In another embodiment, the first communication circuit may receive power from its host unit, such as via the conductors of a lead. According to another aspect of the system, the first communication circuit may include a receiver as well as a transmitter to receive data signals from an external source. This allows the first communication circuit to be programmed with identification, calibration, and other data at the time of component manufacture.

DESCRIPTION OF THE PREFERRED EMBODIMENTS

Figure 1:
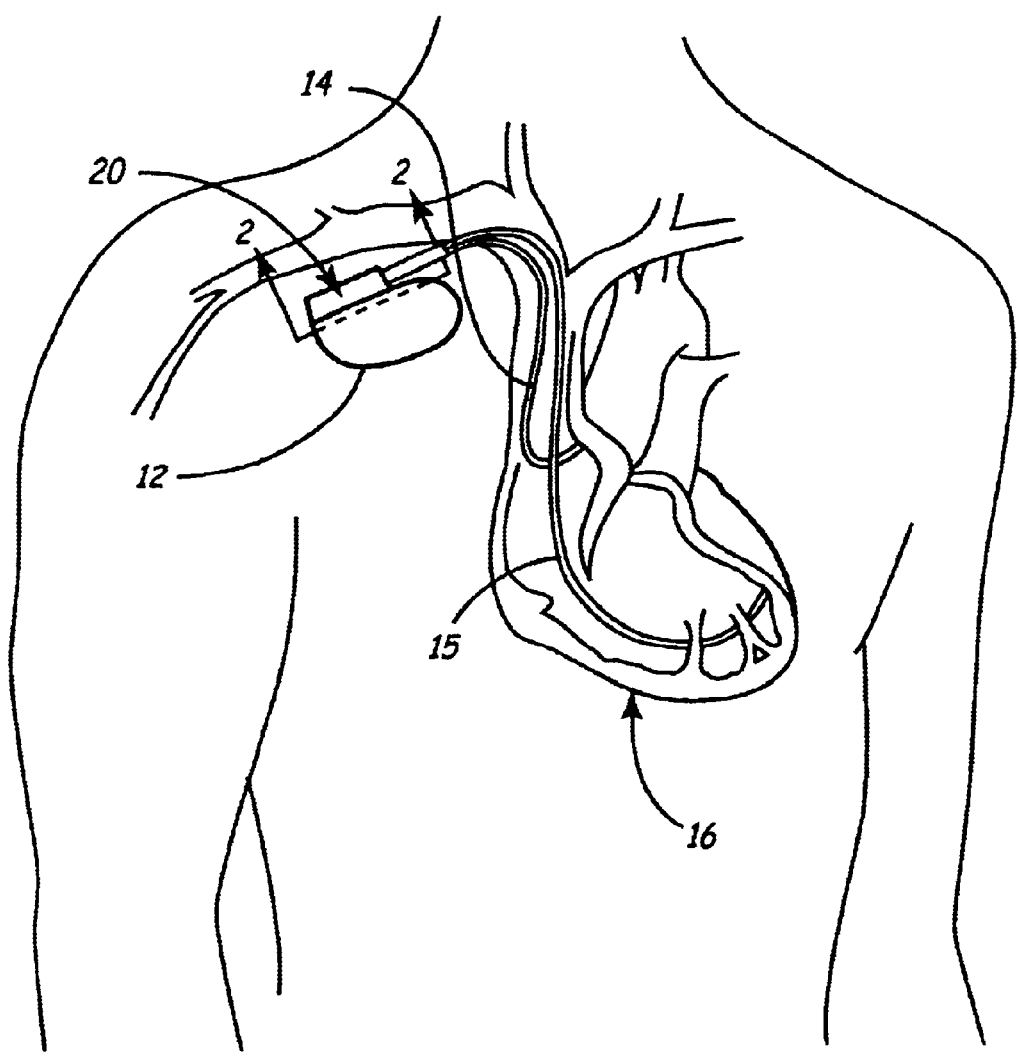
FIG. 1 is a schematic view of an implantable medical device (IMD) implanted within a body.

FIG. 1 is a schematic view of an implantable medical device (IMD) 12 implanted within a body. Leads 14 and 15 are shown coupled to the connector assembly 20 of IMD 12 using one or more feedthroughs. IMD 12, which may be implanted near a human heart 16 or at another location in the body, may be a pacemaker, cardioverter/defibrillator, drug delivery device, brain stimulator, gastric stimulator, nerve stimulator, or any other implantable device. For example, implantable medical device 12 may be an implantable cardiac pacemaker such as that described in U.S. Pat. No. 5,158,078 to Bennett et al., U.S. Pat. No. 5,312,453 to Shelton et al., or U.S. Pat. No. 5,144,949 to Olson et al. Alternatively, IMD 12 may be a pacemaker-cardioverter-defibrillator (PCD) such as those described in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker, et al. As yet another example, IMD 12 may be an implantable neuro-stimulator or muscle stimulator such as those disclosed in U.S. Pat. No. 5,199,428 to Obel et al., U.S. Pat. No. 5,207,218 to Carpentier et al., or U.S. Pat. No. 5,330,507 to Schwartz. The IMD may also be an implantable monitoring device such as that disclosed in U.S. Pat. No. 5,331,966 to Bennett et al., wherein all of the foregoing patents are incorporated by reference herein in their respective entireties.

Figure 2:
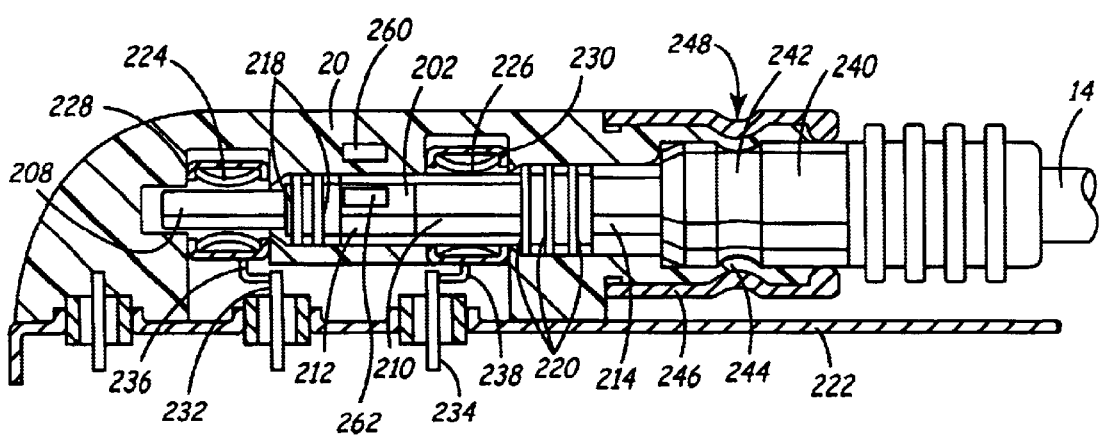
FIG. 2 is a side cutaway view of an exemplary in-line connector assembly at line 2—2 of FIG. 1

FIG. 2 is a side cutaway view of an exemplary in-line connector assembly 20 at line 2—2 of FIG. 1. The connector assembly is shown coupled to a proximal end of lead 14. Connector assembly 20 employs a "setscrewless" lead retainer, and a stepped lumen 202 that receives a connector pin mounted to the proximal end of lead 14. The connector pin includes two conductive connector surfaces 208 and 210, and two insulative areas 212 and 214. Insulative areas 212 and 214 are each provided with a plurality of sealing rings 218 and 220 to seal lumen 202 against fluid entry and to provide a seal intermediate conductive areas 208 and 210. Conductive area 208 may take the form of a metallic, cylindrical pin. Conductive area 210 is illustrated as a metal cylinder.

Connector assembly 20 is shown mounted to the outer enclosure 222 of IMD 12. Connection between the implantable pacemaker and the lead 14 is made by means of spring members 224 and 226, which are mounted in conductive ferrules 228 and 230, respectively. Ferrules 228 and 230 are metal cylinders having central bores and associated internal circumferential grooves that retain the spring members 224 and 226. When inserted, spring members 224 and 226 provide for electrical coupling. Ferrules 228 and 230 are coupled to feedthrough wires 232 and 234 by means of wires 236 and 238, respectively.

The proximal end of lead 14 is shown provided with a cylindrical plastic member 240 that includes a circumferential groove 242 that mates with a deflectable beam lead retainer 244 provided at the distal end of the connector assembly 20. In the embodiment shown, the lead retainer 244 is integrally molded to connector module 20, although the retainer may also be fabricated separately. Surrounding the deflectable lead retainer 244 is an insulative boot 246, which in turn, is surrounded by a suture 248 that acts as a lock to prevent expansion of the deflectable beam retainer 244 to retain lead 14 within connector assembly 20.

The proximal end of lead 14 further includes a first and second communication circuit, which in this embodiment are a passive transponder 262 adapted to communicate with transmitter/receiver 260, respectively. This communication may be facilitated by RF transmissions as substantially described in U.S. Pat. Nos. 4,730,188, 5,041,826, and 5,166,676 to Milheiser, U.S. Pat. No. 5,025,550 to Zirbes, or U.S. Pat. Nos. 5,223,851 and 5,281,855 to Hadden, incorporated herein by reference in their entireties. As noted in the foregoing patents, such passive transponders include an energy coupler for wirelessly coupling electromagnetic, ultrasonic, or optical energy, for example, that is provided by a remote energy source. In one embodiment of the current invention, the energy source is provided by transmitter/receiver 260. Energy may also be provided by another circuit in the IMD. Passive transponder 262 further includes a communication circuit powered by the energy received from the remote energy source, and that is adapted to transfer a signal indicative of identification data stored within the transponder. This will be discussed further below.

It may be noted that the connector assembly 20 shown in FIG. 2 is exemplary only, and many other types of connector assemblies and lead connector types including in-line or bifurcated lead connectors and connector assembly configurations may be utilized.

Figures 3, 4:
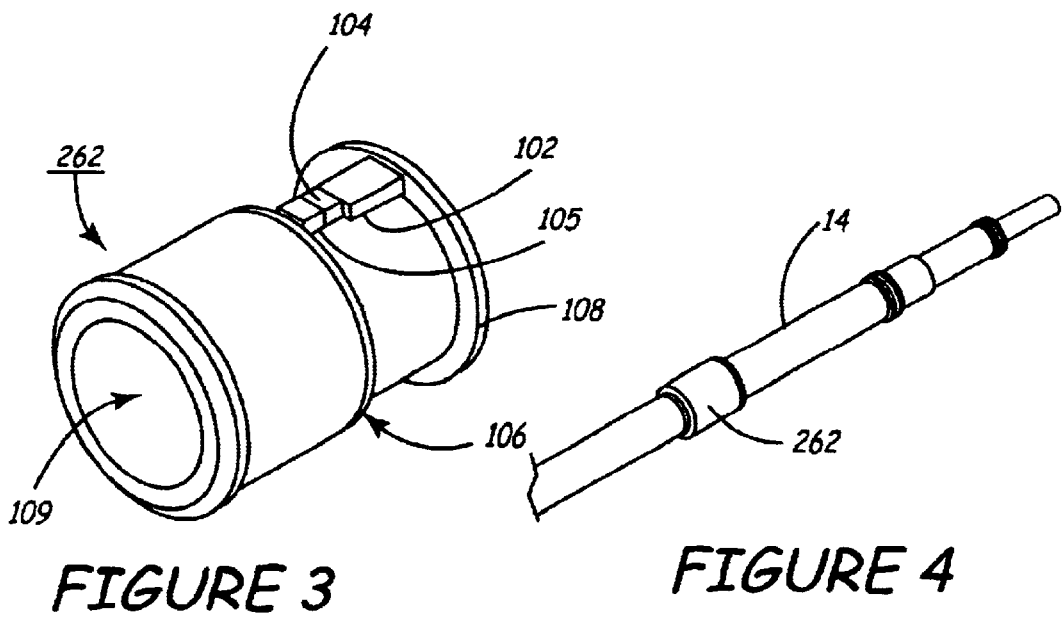
FIG. 3 is a side perspective view of one embodiment of passive transponder of FIG. 2.
FIG. 4 is a side perspective view illustrating a sealed transponder coupled to a lead.

FIG. 3 is a side perspective view of one embodiment of passive transponder 262 of FIG. 2. The transponder includes a wire coil antenna 106 encircling bobbin 108. This antenna may be tuned to the frequency of the carrier signal using an RLC tuned resonant circuit including capacitor 105 to allow for more efficient signal transmission. The center of bobbin 108 includes a lumen 109 to receive a lead. An integrated circuit 102 containing RF receiver/transmitter circuitry may be mounted on bobbin 108. A hermetic cylindrical cover (not shown in FIG. 3) seals the transponder 262 in a manner described in U.S. Pat. No. 5,782,891 to Donders, incorporated herein by reference in its entirety. FIG. 3 further illustrates a surface acoustic wave (SAW) filter 104 to filter signals transmitted by the RF receiver/transmitter circuitry in a manner described further below.

FIG. 4 is a side perspective view illustrating a sealed transponder 262 coupled to lead 14. The sealed transponder 262 may be inserted under a connector sleeve (not shown in FIG. 4) and backfilled with medical adhesive. It may be noted that the transponder of FIG. 3 may be coupled to the lead in many other ways. For example, in another embodiment, the transponder may be fully integrated within the lead body instead of being provided as a separate component.

Figure 5:
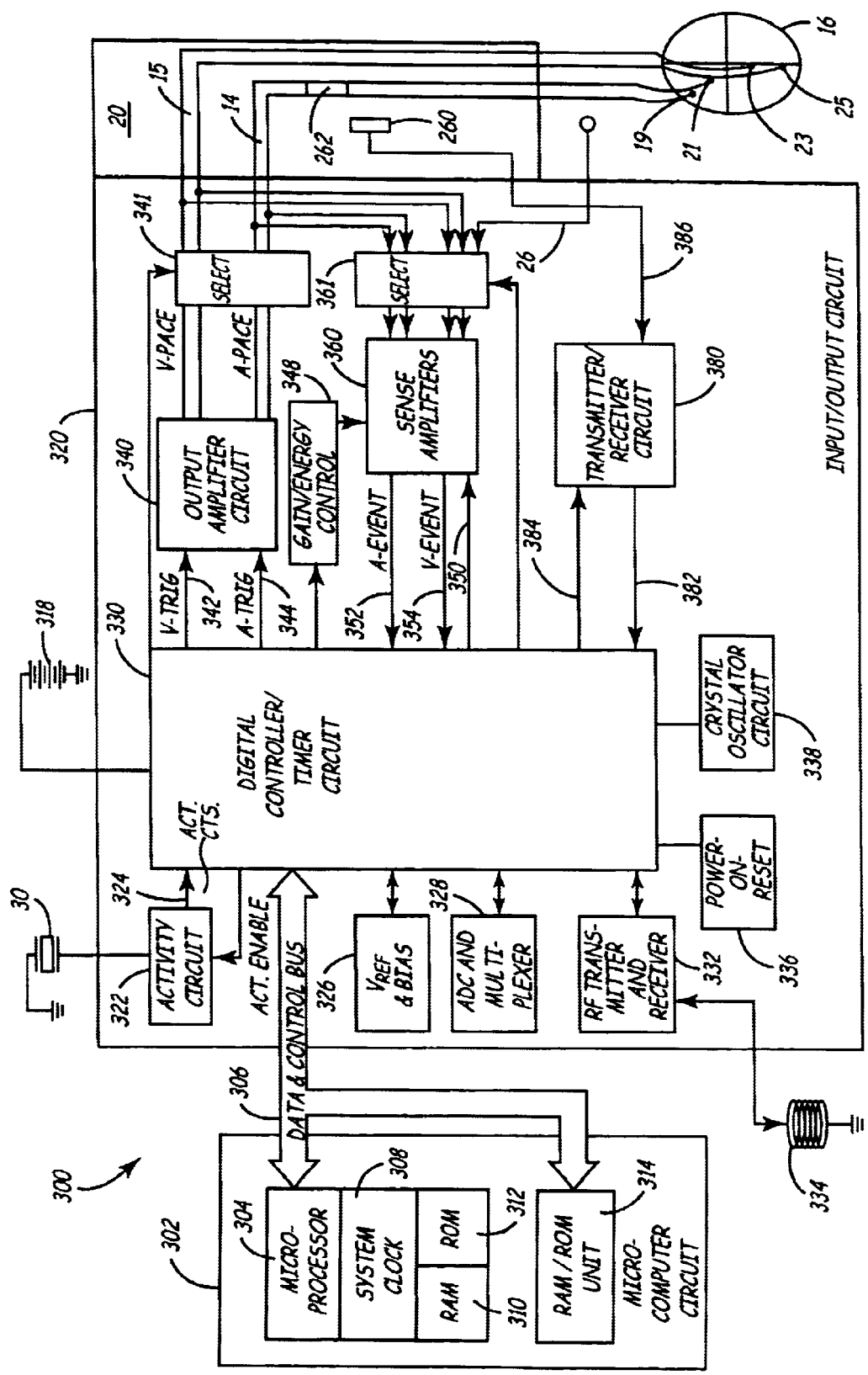
FIG. 5 is a system block diagram of one embodiment of an IMD that may utilize the current invention.

FIG. 5 is a system block diagram of one embodiment of an IMD that may utilize the current invention. IMD 300 is provided with an input/output circuit 320 to sense physiological signals and/or to provide electrical stimulation to a patient. If IMD 300 is a pacemaker, input/output circuit 320 may provide all of the basic timing, stimulation and sensing functions of a DDD or DDDR of a commercially-available pacing device.

Input/output circuit 320 provides the control functions of the IMD. For example, digital controller/timer 330, which receives a clock signal from crystal oscillator circuit 338, generates the appropriate timing and control sequences for the rest of the IMD. Battery 318 provides power for all the components of the IMD, and power-on-reset circuit 336 defines an initial operating condition and also resets the operative state of the device in response to detection of a low battery condition. Reference mode circuit 326 generates stable voltage and currents references for the analog circuits within input/output circuit 320.

FIG. 5 also illustrates leads 14 and 15 coupled to IMD 300. Additional leads\catheters such as exemplary lead 26 may further be implanted within the body for sensing signals and/or for providing electrical stimulation or drug therapy in a manner to be discussed below.

One or more of these leads may carry one or more electrodes. Lead 14, which may be an atrial bipolar pacing lead, is shown carrying two electrodes 19 and 21 positioned in the right atrium of heart 16. Electrodes 19 and 21 may be used both to sense and pace the atrium in a manner well known in the art. Similarly, lead 15 represents a ventricular bipolar lead that may carry two electrodes 23 and 25 implanted in the right ventricle of the heart 16. As discussed above in conjunction with atrial lead 14, electrodes 23 and 25 may be used to sense and pace the ventricle in a manner well known in the art.

In addition to electrodes, one or more other types of sensors of any type known in the art for sensing physiological signals may also be carried on one or more of the leads. For example, sensors may be provided to measure oxygen saturation, change in pressure dP/dT, temperature, minute ventilation or respiration rate. Exemplary sensor systems are described in U.S. Pat. No. 5,154,170 to Bennett et al., U.S. Pat. No. 5,144,524 to Reuter, U.S. Pat. No. 5,271,395 to Wahlstrand, and U.S. Pat. No. 4,485,813 to Anderson.

Analog signals sensed by any of the sensors and/or electrodes may be provided to a programmable electronic switch such as selection circuit 361 to be described further below. The selected signals are provided to sense amplifiers 360. The gain of sense amplifiers 360 may be controlled via controller/timer circuit 330 via gain/energy control 348. The amplified analog signals are received by controller/timer circuit, and provided to analog-to-digital converter (ADC) and multiplexor circuit 328. The ADC digitizes the analog signals so that the signals may be stored and/or transferred to an external device such as a programmer.

Transmission of signals to an external device is accomplished via RF transmitter/receiver circuit 332 and a telemetry antenna 334. The RF transmitter/receiver circuit 332 demodulates received downlink telemetry communications and transmits uplink telemetry data. An exemplary circuit for demodulating and decoding downlink telemetry may correspond to that disclosed in U.S. Pat. No. 4,556,063, while uplink telemetry functions may be provided according to U.S. Pat. Nos. 5,127,404 and 4,374,382. Uplink telemetry capabilities will typically include the ability to transmit stored digital information as well as physiological signals sensed in real-time as described in the '404 patent. It may also be capable of transmitting marker signals indicating the occurrence of sensed and paced depolarizations in the atrium and ventricle, as disclosed in the cited '382 patent.

IMD 300 further includes a microcomputer circuit 302. This circuit controls the operational functions of digital controller/timer circuit 330 via data and control bus 306 by specifying, for example, which timing intervals are employed for performing pacing and sensing functions. Microcomputer 302 may include a microprocessor 304 and associated system clock 308 and on-board processor RAM and ROM 310 and 312, respectively. In addition, microcomputer circuit 302 may include an additional storage unit such as RAM/ROM circuit 314 to provide additional memory capacity. Microprocessor 304 may be interrupt driven, operating in a reduced power consumption mode normally, and awakened in response to defined interrupt events, which may include sensed physiological signals.

In addition to interfacing to microcomputer 302, controller/timer 330 further interfaces directly or indirectly with a battery 318, an activity sensor 30, a telemetry antenna 334, and various feedthroughs (not shown in FIG. 5) to the lead connector elements included in connector assembly 20 discussed above. A piezoelectric crystal activity sensor 30 may be provided to generate electrical pressure wave signals in response to sensed physical activity. The generated signal is processed by activity circuit 322, which, in turn, provides activity signal 324 to digital controller/timer circuit 330. Activity circuit 322 and associated activity sensor 30 may correspond to the circuit and sensor disclosed in U.S. Pat. No. 5,052,388 to Sivula et al., incorporated herein by reference in its entirety.

IMD 300 also includes an output amplifier circuit 340 to provide electrical stimulation to heart 16 via one or more of electrodes 23 and 25 on lead 18V, as well as one or more of electrodes 19 and 21 located on lead 18A. In order to trigger generation of a ventricular pacing or V-PACE pulse, digital controller/timer circuit 330 generates a trigger signal on V-TRIG line 342. Similarly, in order to trigger an atrial pacing or A-PACE pulse, digital controller/timer circuit 330 generates a trigger pulse on A-TRIG line 344. The A-PACE and V-PACE pulse energies may be controlled in pulse width and/or amplitude by gain/energy control 348 which receives a pace energy command signal from digital timer/controller circuit 330. The timing of pacing signals may be controlled based on programmable rate-response features that take into consideration one or more measured physiological parameters as known in the art. Digital controller/timer circuit 330 defines the pacing or escape intervals used to pace the atrium and ventricle using any of the sensing and timing mechanisms known in the art. The signals generated by output amplifier circuit may be provided to a programmable switch such as selection circuit 341, which is programmed by controller/timer 330 in a manner to be discussed below.

In the current embodiment, controller/timer circuit is further shown coupled to transmitter/receiver 380, which, in turn, is coupled via connection 386 to RF antenna 260. This antenna transmits energy to passive transponder 262 carried on lead 14. The energy, which may be optical, electromagnetic, or ultrasonic, for example, is used to power circuitry within passive transponder 262 such that the transponder initiates a data transfer operation to the transmitter/receiver 380. This transferred data may include lead and sensor identification information stored by the transponder and used by IMD 12 to configure the system in a manner to be discussed further below.

In one embodiment, transmitter/receiver 380 decodes data received from the transponder 262, and provides this data to digital controller/timer circuit 330 for subsequent storage in RAM/ROM unit 314. The data may also be transmitted to an external programmer 420 (not shown in FIG. 5) via antenna 334. Digital controller/timer circuit 330 may initiate an interrogation of the transponder following lead implant detection via antenna 260. Lead implant detection may be performed as described in U.S. Pat. No. 5,534,018 and 6,016,447 to Wahlstrand and Juran, respectively, incorporated herein by reference in their entireties.

It may be noted that although FIG. 5 illustrates transmitter/receiver circuit 380 as being a separate circuit as compared to transmitter/receiver 332, the two circuits may be included as a single circuit providing both the ability to transfer and receive data to/from an outside device, and to further receive and/or transmit data from one or more transponders such as transponder 262.

Figure 6:
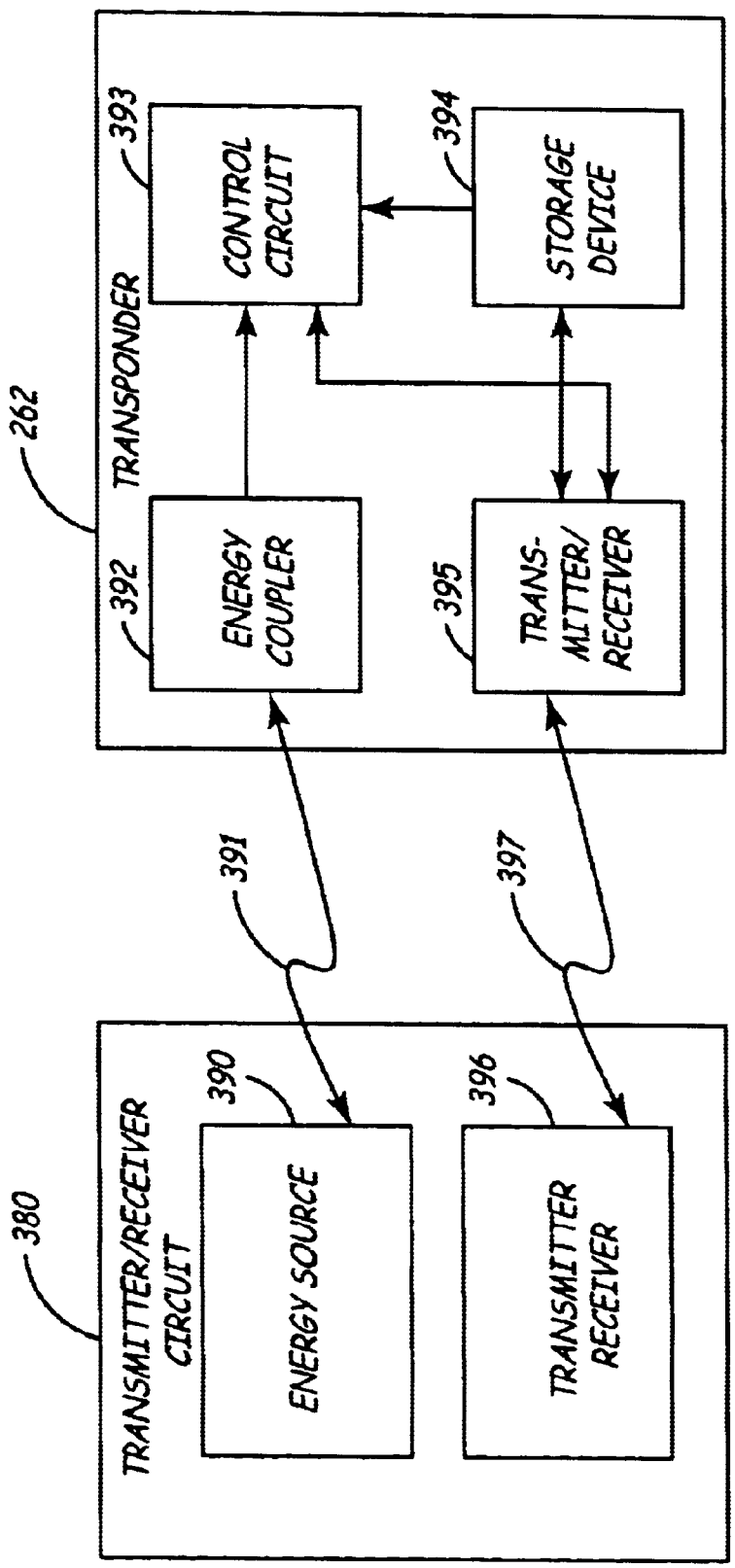
FIG. 6 is a circuit block diagram illustrating in more detail exemplary components of the transponder and transmitter/receiver circuit of FIG. 5.

FIG. 6 is a circuit block diagram illustrating in more detail exemplary components of transponder 262 and transmitter/receiver circuit 380 of FIG. 5. Transmitter/Receiver 380 includes an energy source 390, which may be an inductive circuit, or a photoelectric or piezoelectric transducer to generate electromagnetic, ultrasonic, or optical energy, respectively, as represented by line 391. This energy is received by energy coupler 392, which generates the current and voltage levels needed to power the rest of transponder 262. Transponder includes a control circuit 393, which is coupled to a non-volatile storage device 394. The non-volatile storage device may be a switch device, or any other type of non-volatile storage device known in the art, including a read-only memory (ROM). One or more data values indicative of device type, device technical information, and/or device configuration information may be stored in storage device 394 and read by control circuit 393. The control circuit 393 provides this information to transmitter/receiver 395, which transmits the data via an RF or other type of communication to transmitter/receiver 396. This transmission is indicated by line 397.

Transmitter/Receiver 380 further includes a transmitter/receiver 396 that may provide an unmodulated carrier signal to transmitter/receiver 395. Transmitter/receiver 395 has a tuned resonant circuit as discussed above for resonating at the frequency of the carrier signal to re-transmit a signal at the carrier frequency. The transmitter/receiver 395 also includes means for superimposing an information signal on the re-transmitted signal by modulating the carrier or harmonies of the carrier to reflect the information stored by storage device 394. It may be noted that in an alternative embodiment, the signal provided by the transmitter/receiver 396 is used both as the energy source and the carrier signal such that energy source 390 is not needed.

In one embodiment of the invention, transmitter/receiver 395 may be programmed with information from an external transmitter/receiver circuit at the time of manufacture. This information may include model and serial numbers, lot numbers, expiration dates, electrical characteristics, labeling changes, cautions, product performance results, recall information, and shipping information such a freight IDs and the like. The transponder could further be programmed to store intended therapy information, indications for use, and calibration parameters. All, or portions of, associated technical manuals may be downloaded to the transponder as permitted by the capacity of the storage device.

If transponder is capable of receiving data from an external device in the manner discussed above, data stored within the IMD may be loaded into storage device 394. For example, storage device 394 may store the therapy settings and/or any programmable parameters used to calibrate the IMD for a specific patient. These stored settings and parameters could then be automatically uploaded from transponder 362 following a replacement procedure during which the patient receives a new IMD. This saves time, since manual intervention is not required to configure the newly-implanted device. Other information may likewise be downloaded to transponder 362, including general patient information and health history, and information associated with drug therapies that may or may not be coordinated with the therapy provided by the IMD. In one embodiment, a physician may store information such as threshold values, lead or other impedance values, and/or additional operational and diagnostic information that are determined either at the time of implant, or during subsequent patient visits.

Returning now to FIG. 5, use of the lead identification and configuration information is discussed further. Information from one or more transponders such as transponder 262 may be obtained by the input/output circuit 320 in the manner discussed above. This information may be stored in memory of the IMD such as memory within microcomputer circuit 302. The data may also be transferred to an external device for storage with patient record data. This information may be analyzed by microcomputer circuit 302 or an external processor to automatically configure the IMD. For example, this data can be used by the processor to adjust gain/energy control circuit 348 in a manner that controls the gains of output amplifier circuit 340 and sense amplifiers 360. The adjustments may be based on the type of leads and sensors that are detected in the system. According to one aspect of the system, in the event a particular lead or sensor is not present, unused functions within the IMD may be placed in a low-power mode to conserve battery power.

The ability to adjust the gain associated with a sensed signal is important for several reasons. Physiological sensors such as pressure, temperature, oxygen saturation, or any of the other sensors types known in the art to measure physiological parameters often have operating parameters that vary widely. This is a result of variable conditions that occur during the manufacturing process, as well as differences associated with materials used during production. Therefore, different sensors of the same type may have significantly different scale factors, offsets, and gains. One way to compensate for such variability involves performing a test at the time of implant. A physician may test sensor operation and calibrate the sensor to account for the variable factors. A system and method for performing this type of calibration is described in U.S. Pat. No. 5,919,221. This type of calibration procedure may be time-consuming and error prone, however.

According to the current invention, sensors may be tested at the time of manufacture to determine specific operating parameters. These parameters may then be stored in transponder storage device 394, which may be carried on the sensor lead or the sensor itself. These parameters may be transferred to an IMD in the manner discussed above for use in automatically adjusting sensor gains to account for the sensor differences, and may be further used to adjust and calibrate the IMD functions associated with the sensors. For example, sensor output could be calibrated if an active sensor is being utilized. Such parameters may also be used by a data processing system such as microcomputer 302 to adjust digital values derived from the measured sensor signals. This eliminates the need for human intervention.

Information gained from the transponder may also be used by controller/timer 330 to control selection circuits 361 and 341. For example, the signals provided to sense amplifiers 360 may be selected by selection circuit 361 based on the leads and/or sensors being used by a particular system. Similarly, the signals that are driven by output amplifier circuit 340 may be selected by selection circuit 341 based on whether a lead or a particular electrode is available within the system, and is being used to provide therapy for a given patient. The selection circuits thereby provide "plug-and-play" capabilities for the IMD connector block based on the devices that are sensed within the system.

Information provided by the transponder may further be used to select the configuration of switchable circuits such as those described in U.S. Pat. No. 4,665,919 to Mensink, incorporated herein by reference in its entirety. The configuration of the switchable circuits controls one or more operating parameters of the device, such as input amplifier parameters and filter settings and sensitivity. This configuration can be modified based on the type of components available within the system as indicated by data stored in one or more of transponder circuits 362.

The uses of the configuration and calibration data discussed above are exemplary only, and it will be understood that such data may be used in many other ways to program or automatically calibrate electronic circuitry associated with an IMD or an external device used with the IMD.

Figure 7:
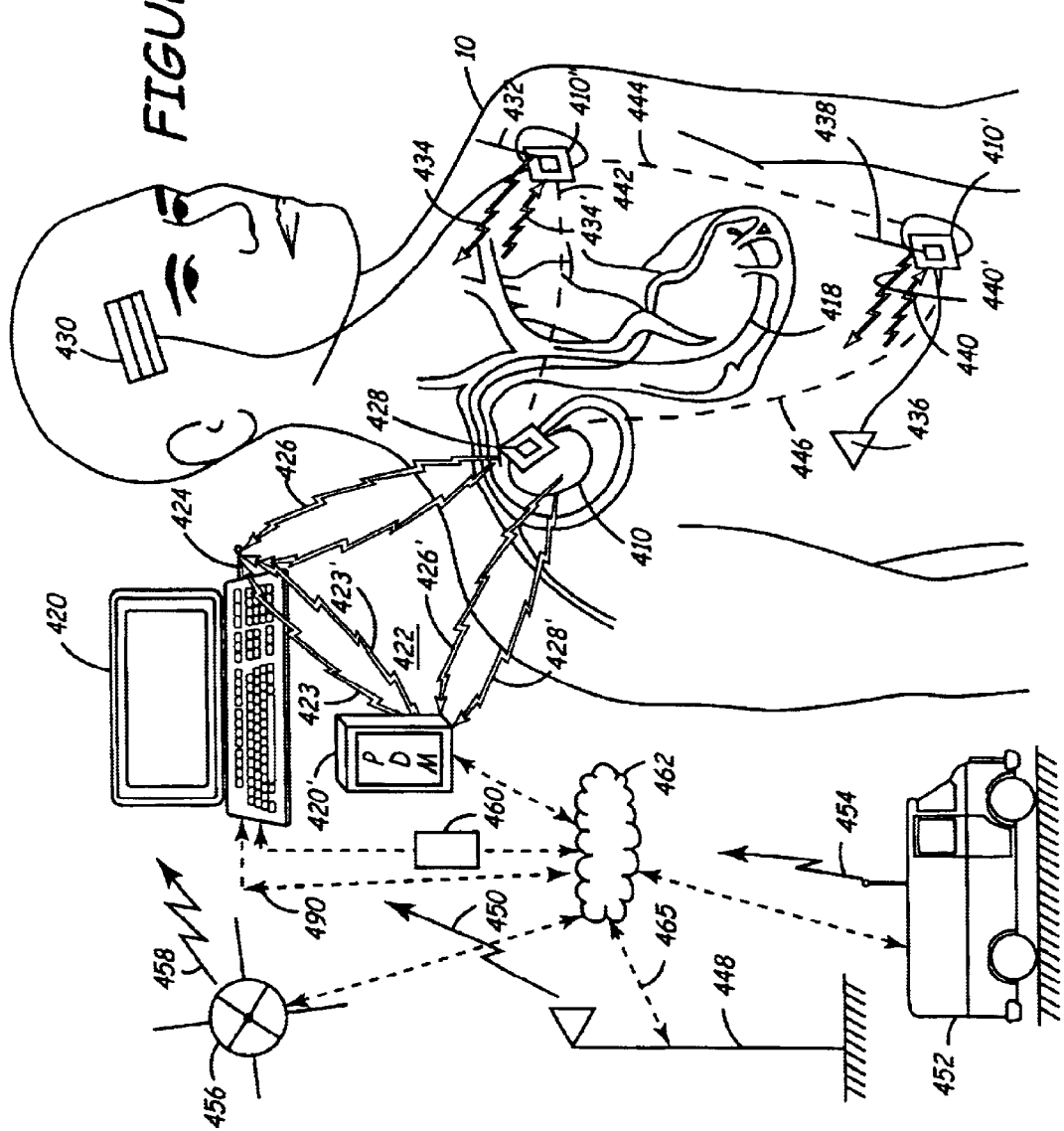
FIG. 7 is a system block diagram illustrating additional embodiments of the present invention.

FIG. 7 is a system block diagram of additional embodiments of the present invention. Specifically, a bi-directional wireless communications system between programmer 420, personal data management (PDM) unit 420' and a number of implantable medical devices (IMDS) represented by IMD 410, IMD 410' and IMD 410" is shown. The IMDs are implanted in patient 10 beneath the skin or muscle. The IMDs are electrically coupled to electrodes 418, 430, and 436 respectively in a manner known in the art. IMD 410 may include a microprocessor for timing, sensing and pacing functions consistent with preset programmed functions as discussed above. Similarly, IMDs 410' and 410" may be microprocessor-based to provide timing and sensing functions to execute the clinical functions for which they are employed. For example, IMD 410' could provide neural stimulation to the brain via electrode 430 and IMD 410", and/or may function as a drug delivery system that is controlled by electrode 436.

The various functions of the IMDs may be coordinated using wireless telemetry. Wireless links 442, 444 and 446 jointly and severally couple IMDs 410, 410' and 410" such that programmer 420 may transmit commands or data to any or all the of IMDs via one of telemetry antennas 428, 432 and 438. This configuration provides a highly flexible and economical wireless communications system between the IMDS. Further, the structure provides a redundant communications system, which enables access to any one of a multiplicity of IMDs in the event of a malfunction of one or two of antennas 428, 432 and 438.

Programming commands or data are transmitted from programmer 420 to IMDs 410, 410' and 410" via external RF telemetry antenna 424. Telemetry antenna 424 may be an RF head or equivalent. Antenna 424 may be located on programmer 420 externally on the case or housing. Telemetry antenna 424 is generally telescoping and may be adjustable on the case of programmer 420. Both programmer 420 and PDM unit 420' may be placed a few feet away from patient 10 and would still be within range to wirelessly communicate with telemetry antennas 428, 432 and 438.

In one embodiment, a remote web-based expert data center 462 may be accomplished through programmer 420 or PDM unit 420'. Accordingly, programmer 420 and PDM unit 420' function as an interface between IMDs 410, 410' and 410" and data center 462. One of the many distinguishing elements of the present invention includes the use of various scalable, reliable and high-speed wireless communication systems to bi-directionally transmit high fidelity digital/analog data between programmer 420 and data center 462.

There are a variety of wireless mediums through which data communications could be established between programmer 420 or PDM unit 420' and data center 462. The communications link between programmer 420 or PDM unit 420' and data center 462 could be modem 460, which is connected both to programmer 420 and to data center 462.

Alternative data transmission systems include, without limitations, stationary microwave and/or RF antennas 448 being wirelessly connected to programmer 420 via tunable frequency wave 450, and with data center 462 via wireless link 465. Similarly, PDM unit 420', mobile vehicle 452, and satellite 456 are in communications with data center 462 via similar wireless links. Further, mobile system 452 and satellite 456 are in wireless communications with programmer 420 or PDM unit 420' via tunable frequency waves 454 and 458, respectively.

In one embodiment, a telnet system may be used to wirelessly access data center 462. Telnet emulates a client/server model and requires that the client run dedicated software to access data center 462. The telnet scheme may employ various operating systems including UNIX, Macintosh, and all versions of Windows.

Using the system shown in FIG. 6, an operator at programmer 420 or data center 462 may initiate remote contact with any of the implanted devices via link antennas 428, 432 and 438 to enable data reception and transmission. For example, an operator or a clinician at data center 462 may downlink to programmer 420 to perform a routine evaluation of programmer 420. If a downlink is required from programmer 420 to IMD 410 for example, the downlink is affected using telemetry antenna 422. In the alternate, if an uplink is initiated from patient 10 to programmer 420, the uplink is executed via wireless link 426.

Each antenna from the IMDs can be used to uplink all or one of the IMDs to programmer 420. For example, IMD 410", which relates to neural implant 430, can be implemented to up-link, via wireless antenna 434 or wireless antenna 434', any one, two or more IMDs to programmer 420. Preferably bluetooth or equivalent chips, adopted to function within a body and which result in low current drain, are included in the IMD to provide wireless and seamless connections 442, 444 and 446 between IMDs 410, 410' and 410". The communication scheme is designed to be broadband compatible and capable of simultaneously supporting multiple information sets and architecture, transmitting at relatively high speed, to provide data, sound and video services on demand.

The various communication paths as shown in FIG. 6 allow lead identification and sensor configuration data to be uploaded to either programmer 420, or to data center 462. Specifically, in the system of FIG. 6, a transmitter/receiver such as transmitter/receiver 380 (FIG. 5) may be resident in programmer 420. This transmitter/receiver may interrogate transponders provided on one or more of the leads to determine lead types, serial numbers, and any available sensor calibration values in a manner similar to that described above. The transfer of information from the transponders may be performed using data encryption technology as described in the co-pending application entitled "Method and Apparatus to Secure Data Transfer from Medical Device Systems", Ser. No. 09/431,881 filed Nov. 2, 1999 by Nichols and incorporated herein by reference. Information that is gained during the interrogation may be entered and stored into a patient record either within the memory of programmer 420, or at data center 462. The information may further be employed to configure one or more IMD functions or systems automatically based on lead types, and/or may also be used to calibrate sensor circuits in ways similar to those discussed above.

In yet another embodiment, a transmitter/receiver such as transmitter/receiver 380 (FIG. 5) may instead be resident in PDM 420'. This transmitter/receiver may interrogate all lead components interconnected to the various IMDs to determine lead types, serial numbers, any sensor calibration values, and to communicate this information to programmer 420. Programmer may then program any or all of the IMDs to properly configure the IMD configurations. Alternatively, this configuration function may be performed by the processing circuit associated with each IMD.

The foregoing examples describe several embodiments of the inventive recognition and configuration system and method, although it will be understood that modifications are possible within the scope of the current invention. For example, the foregoing examples discuss a system that is powered using a remote energy source and an energy coupler as shown in FIG. 6. Other types of power systems may be utilized, however. In one instance, transponder 262 is not passive, but instead receives power by loosely coupling off of electrical therapy output of an IMD.

Figure 8:
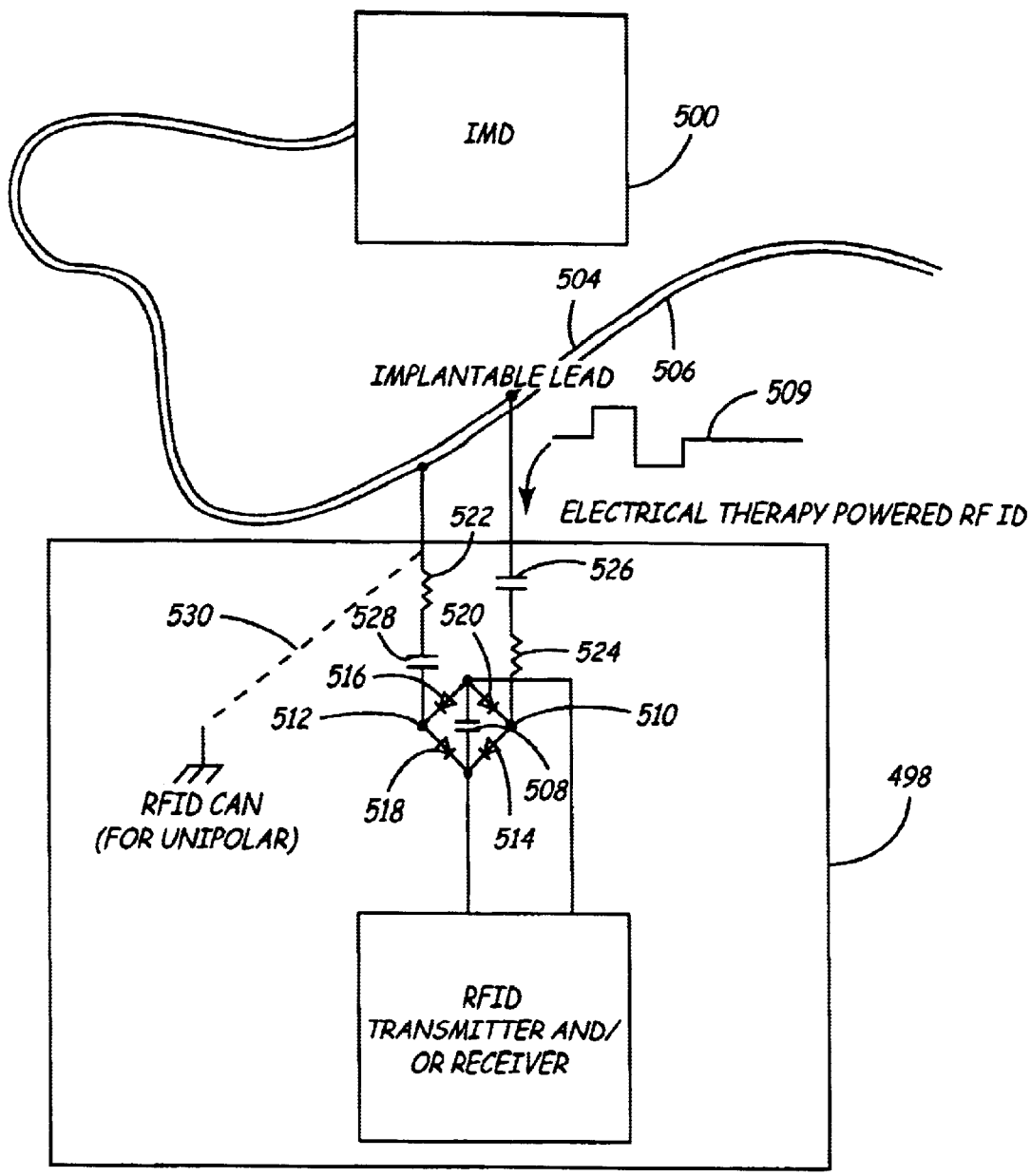
FIG. 8 is a circuit diagram illustrating a transponder coupled to the therapy output energy source of an IMD.

FIG. 8 is a circuit diagram illustrating a transponder 498 coupled to the therapy output energy source of IMD 500. IMD 500 is shown coupled to a lead that includes two conductors 504 and 506. These conductors are coupled to a bridge circuit that includes capacitor 508. This capacitor is charged by one or more pulse signals generated by IMD 500 during, for example, the delivery of pacing therapies or other pulsed stimulation therapies. The pulsed signals 509 include a position and a negative phase such that during a portion of the signal, the voltage at point 510 is more position than at point 512, and in a different portion of the signal, the voltage polarity is reverse. In the former instance, current flows through diodes 514 and 516, and in the later instance current flows through diodes 518 and 520. In both cases, capacitor 510 is charged in the manner shown.

In the preferred embodiment, capacitor 510 is charged by the occurrence of multiple pulsed signals. For example, ten or more pulses may be required to completely charge the capacitor. The values of resistors 522 and 524 are selected to prevent the capacitor circuit from presenting an unduly large load that would affect the therapy delivery of IMD 500. Capacitors 526 and 528 may be provided to prevent a DC offset voltage potential from being present across conductors 504 and 506, which may promote corrosion of any electrodes that are carried by the lead. Finally, it may be noted that if a unipolar lead is employed, the capacitor circuit is coupled to only a single lead conductor, with the second connection being provided via the IMD and transponder cans, as indicated by dashed line 530.

Using the circuit of FIG. 8, transponder 498 may be intermittently operated to provide a brief burst of modulated RF energy from the transmitter of the transponder. In a similar manner, the receiver of the transponder could be intermittently powered to receive information from the IMD or another source. This embodiment would allow for longer-range communications than is provided by the passively-powered embodiment.

Another modification to the current invention involves use of a surface acoustic wave (SAW) filter 104 within the transponder as shown in FIG. 3. This type of filter includes an SAW delay line. An RF signal is transmitted from an interrogation unit such as transmitter/receiver circuit 380 of FIG. 6, and is received by an antenna residing in the transponder that is coupled to the delay line. The signal is provided to the delay line, which includes predetermined discontinuities that result in signal reflections. The unique signal reflections, which are a result of the selected configuration of the delay line, can be interpreted as a signature which may be transmitted to the interrogation unit for interpretation. The signature may encode a serial number, or any other type of information. The SAW filter thereby serves as a nonvolatile storage device not unlike a bard-wired switch. This filter may be used in place of, or in addition to, storage devices such as storage device 394 of FIG. 6.

According to another aspect of the invention, data stored within a transponder 362 of a component is employed by an IMD to configure circuitry within the component. For example, an embodiment of a lead may include data interface to couple to an interface of the IMD. Based on information transferred from a transponder of the lead to the IMD, a processing circuit such as micro-computer circuit 302 is capable of transferring signals via the data interface to configure circuitry of the lead. For example, the processing circuit may store data within a programmable device such as a register provided by the lead, thereby configuring the lead for operation with the IMD.

Other modifications are possible within the scope of the current invention. For example, although the above-described embodiments primarily relate to a transponder attached to, or integrated within, a lead, the invention may be usefully employed to identify other implantable medical devices that may be used in conjunction with the active IMD in the system. For example, pluggable antennas or electrodes that may be selectively coupled to the active IMD may be identified and configured using a mechanism similar to that described herein. Additional components such as heart valves or stents could include similar transponders on the surface of, or integrated within, the device to store information that may then be transferred to external devices that are located within, or outside of, the body. Therefore, while particular embodiments of the present invention have been disclosed, it is to be understood that various different modifications are possible and are contemplated within the scope of the specification, drawings, abstract and appended claims.

What is claimed is:

1. A system to configure an implantable medical device (IMD), comprising:
   an IMD;
   at least one additional component adapted to be coupled to the IMD; the at least one additional component comprising a stimulating electrode;
   a data set descriptive of the at least one additional component; the data set comprising data descriptive of the stimulating electrode;
   a first communication circuit carried on the at least one additional component, the first communication circuit comprising means to store and transmit the data set;
   a second communication circuit in proximity to the first communication circuit comprising means to receive the data set from the first communication circuit; and
   a processing circuit coupled to receive the data set from the second communication circuit, and to configure initial operations of the IMD based on the data set.

2. The system of claim 1, wherein the first communication circuit is a transponder.

3. The system of claim 2, wherein the transponder is a passive transponder.

4. The system of claim 1, wherein the data set further comprises data indicative of component identification information.

5. The system of claim 1, wherein the data set further comprises data included in a technical manual associated with the at least one additional component.

6. The system of claim 1, wherein the at least one additional component further comprises a sensor to sense a physiological parameter, and wherein the data set further comprises data descriptive of the sensor.

7. The system of claim 6, wherein the system further includes means for calibrating the sensor based on the data descriptive of the sensor.

8. The system of claim 1, wherein the at least one additional component further comprises a connector adapted to be coupled to the IMD, and wherein the data set further comprises data descriptive of the connector.

9. The system of claim 1, wherein the second communication circuit is located within the IMD.

10. The system of claim 1, further comprising an external device and wherein the second communication circuit is located in the external device.

11. The system of claim 10, wherein the external device comprises a programmer.

12. The system of claim 10, wherein the external device comprises a patient data module (PDM).

13. The system of claim 1, wherein the means to transmit the data set of the first communication circuit includes an RF transmitter.

14. The system of claim 1, wherein the second communications circuit further comprises means for transmitting information and the first communication circuit further comprises an RF receiver capable of receiving the information from the second communication circuit.

15. The system of claim 14, the first communication circuit further comprises means to store the information received from the second communication circuit.

16. The system of claim 1, wherein the first communication circuit further comprises means for filtering a signal containing the data set, the filtering means including a surface acoustic wave (SAW) filter.

17. The system of claim 1, wherein the IMD includes at least one amplification circuit, and wherein the system further includes a gain adjustment circuit coupled to control the gain of the at least one amplification circuit, and wherein the processing circuit is capable of configuring the gain adjustment circuit based on the data set.

18. The system of claim 1, wherein the system further includes at least one selection circuit coupled to the at least one additional component, and wherein the processing circuit is capable of configuring the selection circuit to control interconnection of the at least one additional component with the IMD based on the data set.

* * * * *

UNITED STATES PATENT AND TRADEMARK OFFICE
CERTIFICATE OF CORRECTION

PATENT NO. : 6,675,049 B2
DATED : January 6, 2004
INVENTOR(S) : David L. Thompson et al.

It is certified that error appears in the above-identified patent and that said Letters Patent is hereby corrected as shown below:

Column 15,
Line 13, after "14," insert -- wherein --.

Signed and Sealed this

Ninth Day of November, 2004

JON W. DUDAS
*Director of the United States Patent and Trademark Office*